United States Patent
Cox (10) Patent No.: US 6,565,603 B2
(45) Date of Patent: May 20, 2003

(54) MITRAL VALVE ANNULOPLASTY RING

(75) Inventor: James L. Cox, McLean, VA (US)

(73) Assignee: Cardiac Concepts, Inc., Little Rock, AR (US)

( * ) Notice: Subject to any disclaimer, the term of this patent is extended or adjusted under 35 U.S.C. 154(b) by 0 days.

(21) Appl. No.: 09/776,124

(22) Filed: Feb. 2, 2001

(65) Prior Publication Data

US 2001/0034551 A1 Oct. 25, 2001

Related U.S. Application Data

(62) Division of application No. 09/399,444, filed on Sep. 17, 1999, now Pat. No. 6,250,308, which is a continuation of application No. 09/097,763, filed on Jun. 16, 1998, now abandoned.

(51) Int. Cl.$^7$ .................................................. A61F 2/06
(52) U.S. Cl. ...................... 623/2.36; 623/2.37; 623/904
(58) Field of Search ............................... 623/2.36, 904, 623/2.37–3.1; 128/898

(56) References Cited

U.S. PATENT DOCUMENTS

| | | |
|---|---|---|
| 3,571,815 A | 3/1971 | Somyk |
| 3,691,567 A | 9/1972 | Cromie |
| 3,714,671 A | 2/1973 | Edwards et al. |
| 3,755,823 A | 9/1973 | Hancock |
| 3,860,005 A | 1/1975 | Anderson et al. |
| 3,983,581 A | 10/1976 | Angell et al. |
| 4,035,849 A | 7/1977 | Angell et al. |
| 4,106,129 A | 8/1978 | Carpentier et al. |
| 4,276,132 A | 6/1981 | Fettel et al. |
| 4,339,831 A | 7/1982 | Johnson |
| 4,343,049 A | 8/1982 | Fettel et al. |
| 4,345,340 A | 8/1982 | Rosen |
| 4,441,216 A | 4/1984 | Ionescu et al. |
| 4,535,483 A | 8/1985 | Klawitter et al. |
| 4,602,911 A | 7/1986 | Ahmadi et al. |
| 4,743,253 A | 5/1988 | Magladry |
| 4,755,181 A | 7/1988 | Igoe |
| 4,816,029 A | 3/1989 | Penny, III et al. |
| 4,851,000 A | 7/1989 | Gupta |
| 4,863,460 A | 9/1989 | Magladry |
| 4,917,698 A | 4/1990 | Carpentier et al. |
| 5,035,709 A | 7/1991 | Wieting et al. |
| 5,041,130 A | 8/1991 | Cosgrove et al. |
| 5,061,277 A * | 10/1991 | Carpentier et al. ........ 623/2.36 |
| 5,071,431 A | 12/1991 | Sauter et al. |
| 5,104,405 A | 4/1992 | Nimni |
| 5,104,407 A * | 4/1992 | Lam et al. ................ 623/2.36 |
| 5,147,370 A | 9/1992 | McNamara et al. |
| 5,163,953 A | 11/1992 | Vince |
| 5,163,954 A | 11/1992 | Curcio et al. |
| 5,178,633 A | 1/1993 | Peters |
| 5,201,880 A | 4/1993 | Wright et al. |
| 5,258,021 A | 11/1993 | Duran |
| 5,306,296 A | 4/1994 | Wright et al. |
| 5,312,341 A * | 5/1994 | Turi ............................ 604/96 |
| 5,350,420 A | 9/1994 | Cosgrove et al. |
| 5,360,014 A | 11/1994 | Sauter et al. |
| 5,376,112 A | 12/1994 | Duran |
| 5,397,346 A | 3/1995 | Walker et al. |
| 5,397,348 A | 3/1995 | Campbell et al. |
| 5,450,860 A * | 9/1995 | O'Connor ................ 128/898 |

(List continued on next page.)

Primary Examiner—Corrine McDermott
Assistant Examiner—Suzette J. Jackson
(74) Attorney, Agent, or Firm—Boyd D. Cox (57) ABSTRACT

A mitral valve annuloplasty ring and method for implanting a mitral valve annuloplasty ring to treat mitral insufficiency by reestablishing the normal shape and contour of the mitral valve annulus. The annuloplasty ring is flexible and can be readily adjusted to different sizes and shapes. The method substantially eliminates scarring subsequent to the annuloplasty procedure to maintain flexibility of the ring and the annulus indefinitely.

20 Claims, 6 Drawing Sheets

U.S. PATENT DOCUMENTS

| | | |
|---|---|---|
| 5,469,868 A | 11/1995 | Reger |
| 5,489,297 A | 2/1996 | Duran |
| 5,489,298 A | 2/1996 | Love et al. |
| 5,578,073 A | 11/1996 | Haimovich et al. |
| D376,206 S | 12/1996 | Reif |
| 5,584,879 A | 12/1996 | Reimold et al. |
| 5,593,424 A * | 1/1997 | Northrup, III .............. 606/232 |
| 5,593,435 A | 1/1997 | Carpentier et al. |
| 5,607,469 A | 3/1997 | Frey |
| 5,607,470 A | 3/1997 | Milo |
| 5,607,471 A * | 3/1997 | Seguin et al. .............. 623/2.36 |
| 5,612,885 A | 3/1997 | Love |
| 5,628,790 A | 5/1997 | Davidson et al. |
| 5,674,279 A | 10/1997 | Wright et al. |
| 5,674,280 A | 10/1997 | Davidson et al. |
| 5,674,390 A | 10/1997 | Matthews et al. |
| 5,776,189 A * | 7/1998 | Khalid ...................... 623/2.36 |
| 5,824,071 A * | 10/1998 | Nelson et al. ................. 604/8 |
| 6,183,512 B1 * | 2/2001 | Howanec, Jr. et al. ..... 623/2.36 |
| 6,250,308 B1 * | 6/2001 | Cox ........................... 128/898 |
| 6,402,781 B1 * | 6/2002 | Langberg et al. .......... 623/2.36 |
| 6,416,548 B2 * | 7/2002 | Chinn et al. ............... 623/2.36 |

\* cited by examiner

MITRAL VALVE ANNULOPLASTY RING

This is a divisional of application Ser. No. 09/399,444 filed Sep. 17, 1999 now U.S. Pat. No. 6,250,308, which is a continuation of Ser. No. 09/097,763 filed Jun. 16, 1998 and now abandoned. The entire disclosures of each of the aforementioned applications are hereby incorporated by reference herein.

BACKGROUND

The present invention is directed to a mitral valve annuloplasty ring to treat mitral insufficiency in a patient. Mitral insufficiency, also known as mitral regurgitation, is a common cardiac abnormality wherein the heart's mitral valve does not properly close.

In a normally functioning heart, oxygenated blood passes from the left atrium through the opened mitral valve and into the left ventricle when the left ventricle is in a relaxed state. When the left ventricle contracts, the blood is pushed out of the left ventricle thereby closing the mitral valve to prevent blood flowing back or regurgitating into the left atrium. From the left ventricle, the oxygenated blood is pumped out of the heart and directed to the rest of the body.

With mitral insufficiency, the mitral valve does not fully close and a portion of blood leaks back into the left atrium when the left ventricle contracts. As a result, the heart has to work harder by pumping not only its regular volume of blood, but also the extra volume of blood that regurgitates back into the left atrium. The added workload creates an undue strain on the left ventricle. This strain can eventually wear out the heart and result in death when the condition is prolonged and severe enough. Consequently, a properly functioning mitral valve is critical to the pumping efficiency of the heart.

Mitral valve annuloplasty is a well known approach for treating mitral insufficiency, although other treatments are used which include replacing the mitral valve, repairing the mitral valve leaflets, and shortening or replacing the chordae tendinae. Mitral valve annuloplasty is the reparation of the mitral valve annulus which effects full closure of the leaflets by reestablishing the size and shape of the normal mitral valve annulus. Such an annuloplasty most commonly incorporates the use of a mitral annuloplasty ring wherein the ring is implanted on the mitral valve annulus.

There are three basic types of mitral annuloplasty rings used in annuloplasty procedures. They include a rigid ring, a flexible ring and a combined ring that has both a flexible component and a rigid component.

Due to their inflexibility, the rigid rings dictate the shape and contour of the mitral valve. The native mitral valve annulus flexes in response to the movement of the heart. However, with a rigid ring the annulus is not able to flex normally or move freely with the pumping action of the heart. As a result of the rigidity, the physiologic factors that normally shape the mitral valve annulus are not allowed to take precedence in shaping the valve.

Another drawback with rigid rings is that they can induce a heart condition known as systolic anterior motion in patients having a mitral valve posterior leaflet that is too "tall". During ventricular contraction, the posterior leaflet pushes the anterior leaflet in a direction opposite to the anterior leaflet's normal movement, resulting in the obstruction of the left ventricle's outflow tract.

Overall, rigid annuloplasty rings do not allow the mitral valve annulus to reestablish its normal shape and form as dictated by the action of the heart pumping. The shape and contour of the annulus is established by the inflexible shape and form of the ring itself.

Flexible rings made of Dacron cloth, unlike the rigid rings, can allow the mitral valve annulus to move and flex as the heart contracts and relaxes. However, several drawbacks still exist. Proper shape and contour of the annulus is necessary in order for the mitral valve leaflets to close effectively. One shortcoming of the flexible ring is its predisposition to crimp during implantation. Crimping can be detrimental to the valve annulus, sometimes resulting in a mitral orifice that is too small. This can lead to stenosis of the valve. Furthermore, neither the flexible rings nor the combined rings will remain flexible indefinitely after annuloplasty. Since the rings are secured in place by a line of sutures attached directly to the annulus, scarring and resultant stiffening of the annulus inevitably develops. This loss of flexibility impedes the normal flexing and movement of the heart, particularly the left ventricle and, therefore, the heart cannot function optimally.

SUMMARY

The annuloplasty ring of the present invention is a combined ring which comprises a first section that is substantially rigid and a second flexible section. The ring can be readily adjusted to fit the annulus of any particular patient. The method of implanting the annuloplasty ring of the present invention comprises installing a ring within the fat pad of the atrioventricular groove which surrounds the mitral valve annulus. The method does not require a series of sutures extending through the mitral valve annulus tissue to hold the ring in place. Resultant scarring and stiffening of the annulus is thereby substantially eliminated.

The ring of the present invention is positioned in the fat pad of the atrioventricular groove adjacent to the mitral valve annulus. The flexible section of the ring extends adjacent to the flexible posterior portion of the annulus, while the rigid section of the ring spans the substantially rigid inter-trigone section of the annulus. Since the flexible section of the ring is held in the atrioventricular groove of the posterior section of the annulus, it is not necessary to suture the flexible section directly to the mitral valve annulus. As a result, scarring of the annulus is substantially eliminated, thereby allowing the ring and annulus to remain flexible indefinitely. As in the normal heart, this flexibility enables the mitral valve annulus to flex in several planes during contraction and relaxation of the heart. The result is better postoperative functioning of the mitral valve and better postoperative functioning of the left ventricle, as well.

It is an object of the present invention to provide an annuloplasty ring that reestablishes the normal shape and contour of the mitral valve annulus.

It is a further object of the invention to provide an annuloplasty ring that is flexible enough to allow the mitral valve and annulus to flex through different planes, yet positioned such that the shape and contour of a normal mitral valve annulus is reestablished.

It is a further object of the present invention to provide a flexible annuloplasty ring that does not crimp during implantation.

It is a further object of the present invention to provide an annuloplasty ring that can be flexed in all manner that the native mitral valve annulus flexes.

It is a further object of the present invention to provide an annuloplasty ring that maintains flexibility of the ring and the mitral valve annulus indefinitely.

It is a further object of the present invention to provide an annuloplasty ring wherein implanting the ring results in effective coaptation of the anterior and posterior leaflets of the mitral valve.

It is a further object of the present invention to provide an annuloplasty ring that does not impede the movement of the left ventricle's base when the ventricle is contracting and relaxing, thereby allowing effective functioning of the left ventricle.

It is a further object of the present invention to provide an annuloplasty ring and a method of surgically implanting an annuloplasty ring that allow the base of the left ventricle to assume its full range of movement when contracting and relaxing to allow effective functioning of the left ventricle.

It is a further object of the present invention to provide an annuloplasty ring that allows the left ventricle to move naturally as the heart pumps and allows the mitral valve annulus to flex freely in response to the movement of the left ventricle.

It is a further object of the present invention to provide an annuloplasty ring that does not require a plurality of sutures along the posterior portion of the mitral valve annulus to secure the ring in place.

It is a further object of the present invention to provide an annuloplasty ring that can be readily adjusted in size.

It is a further object of the present invention to provide an annuloplasty ring that can be readily adjusted in shape by adjusting the circumference of the ring.

It is a further object of the present invention to provide a kit for an annuloplasty ring that reestablishes the normal shape and contour of the mitral valve annulus.

Reference is made to the accompanying drawings in which are shown illustrative embodiment of the invention and from which novel features and advantages will be apparent.

DETAILED DESCRIPTION

The left ventricle is the main pumping chamber of the heart. Oxygenated blood from the lungs enters the left atrium and passes into the left ventricle through the mitral valve. The blood is pumped from the left ventricle to the rest of the body.

As shown in FIGS. 1A–1F, the mitral valve (30) is a one way passive valve comprising a pair of leaflets, including a larger anterior leaflet (32) and a smaller posterior leaflet (33). The leaflets open and close in response to pressure differences in the heart (5) on either side of the mitral valve (30). The base of each anterior (32) and posterior (33) leaflet is attached to the mitral valve annulus (34).

The contour of the mitral valve annulus (34) refers to the outline or form of the annulus (34) when viewed in the general plane of the annulus (34). The shape of the annulus (34) is that shape viewed from the atrial side of the mitral valve (30), "looking down" on the mitral valve annulus (34).

The mitral valve annulus (34) includes a posterior portion (35) and an anterior portion (36). The anterior portion (36), also known as the inter-trigone segment or section, is a generally straight, substantially rigid segment. The posterior portion (35) of the annulus (34) is a flexible, curvilinear segment that encompasses a larger proportion of the annulus circumference than the anterior portion (36). The right (37) and left (38) fibrous trigones mark the ends of the generally straight segment and define the intersection points between the posterior (35) and anterior portions (36).

Figure 2A:
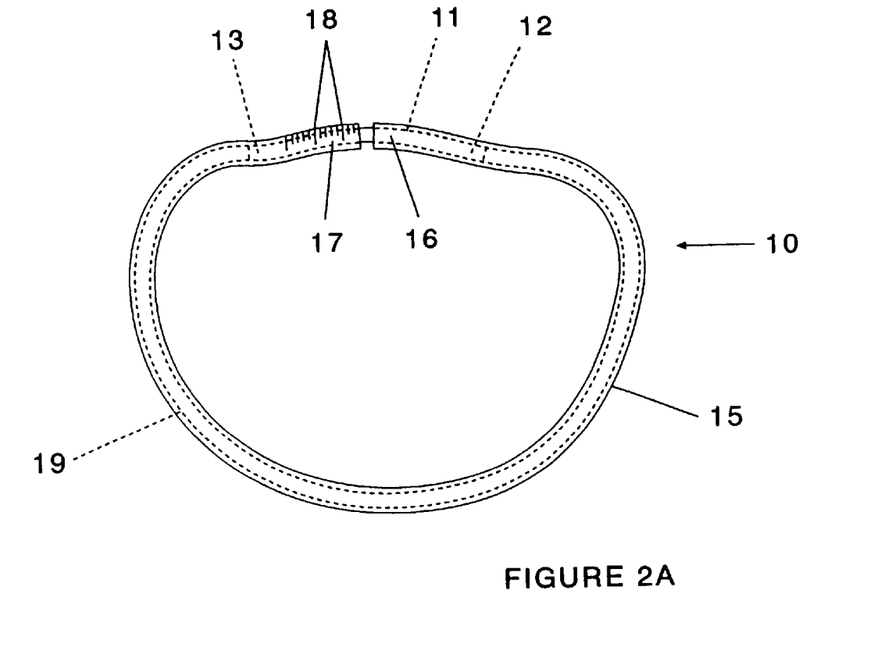
FIG. 2A is a top view of a preferred embodiment of the mitral valve annuloplasty ring of the present invention in a closed configuration.
Figure 2B:
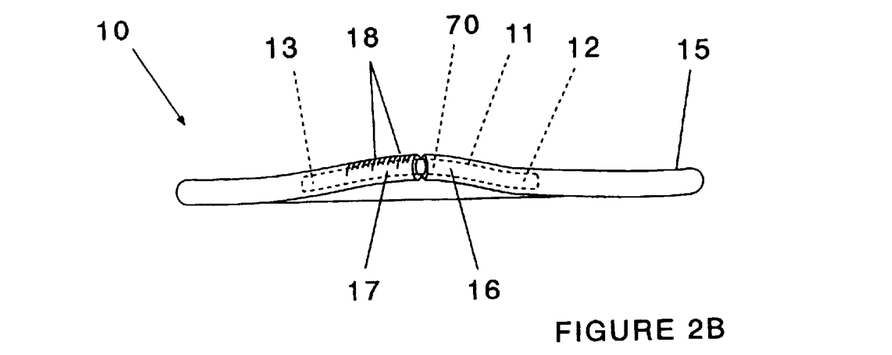
FIG. 2B is a side view of the mitral valve annuloplasty ring in a closed configuration.
Figure 3:
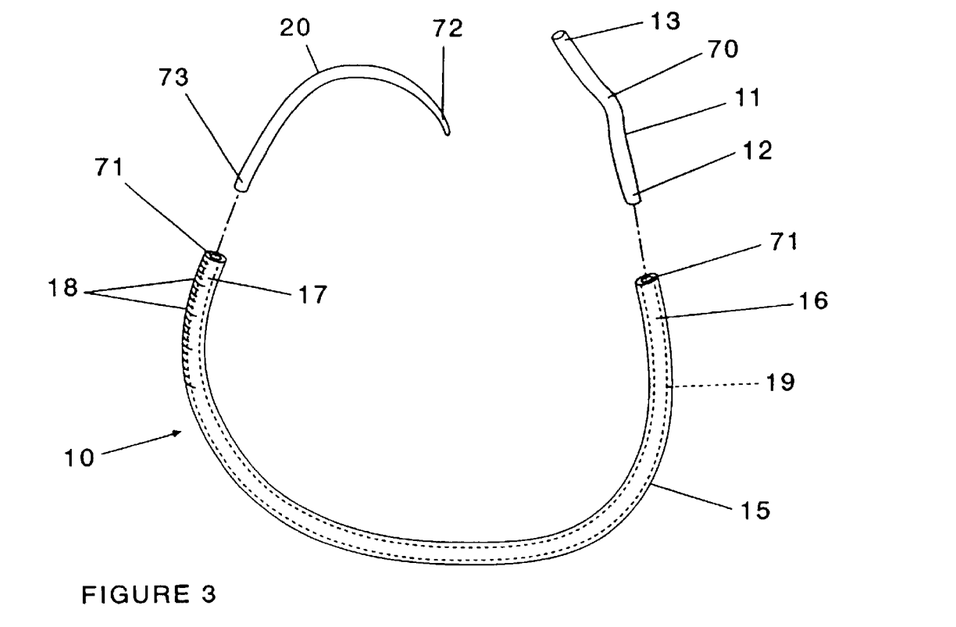
FIG. 3 is an exploded view of the mitral valve annuloplasty ring with needle.

Referring to FIGS. 2A and 2B, there is shown a preferred embodiment of the annuloplasty ring (10) comprising the present invention. The ring (10) comprises a first section (11) and a second section (15). The first section (11) has a first end (12) and a second end (13), while the second section (15) includes a proximal end (16) and a distal end (17). A means for sizing the annuloplasty ring (10) includes measurement indicia (18) extending inwardly from an outermost edge of the second section's distal end (17). The annuloplasty ring (10) also includes a detachable needle (20) having a tip (72) and an attaching end (73) as shown in FIG. 3.

The annuloplasty ring (10) comprises a first means for joining the second end of the first section to the distal end of the second section and a second means for joining the first end of the first section to the proximal end of the second section. The ring (10) also comprises a third means for joining the second end of the second section to the needle.

In one preferred embodiment, the first means for joining the second end of the first section to the distal end of the second section, the second means for joining the first end of the first section to the proximal end of the second section, and the third means for joining the second end of the second section to the needle comprise frictional engagements.

The frictional engagements include a hollow inner portion (19) in the second section (15) having exterior openings (71) at the proximal (16) and distal (17) ends. The hollow inner portion (19) can extend the entire length of the second section (15) or alternately, it can be limited to the ends (16, 17) of the second section (15). The hollow portion (19) has an inner diameter that is approximately equal to the outer diameter of the first (12) and second (13) ends of the first section (11) and also that is approximately equal to the outer diameter of the attaching end (73) of the needle (20).

The exterior openings (71) of the hollow inner portion (19) on the proximal end (16) of the second section (15) receives the first end (12) therein, while the exterior opening (71) of the hollow inner portion (19) on the distal end (17) receives the second end (13) of the first section and, alternately, the attaching end (73) of the needle (20). When the ends (12, 13) of the first section (11) are inserted through the exterior openings (71) into the hollow inner portion (19), a frictional engagement is created between the respective inner and outer diameters which secures the ends of the sections (11, 15) together. Likewise, when the attaching end (73) of the needle (20) is inserted through the exterior opening (71) into the hollow inner portion (19) of the distal end (17), the needle (20) is held within the hollow inner portion (19) by frictional engagement.

Although the first means for joining the second end of the first section to the distal end of the second section, the second means for joining the first end of the first section to the proximal end of the second section, and the third means for joining the second end of the second section to the needle comprise frictional engagements, any suitable and separate types of means could be used instead.

The first (11) and second (15) sections are elongated. In one preferred embodiment, the first section (11) has a bow or bend (70) in the center region. The bow (70) is offset approximately 1.0 mm from a reference plane in which the first (12) and second (13) ends are located. In another preferred embodiment, the first section of the ring is straight and does not have a bow.

The first section (11) is made from a substantially rigid material. It is preferable that the material is able to maintain its rigidity indefinitely and also preferable that it is inert or compatible with body tissues. Examples of materials that could be used for the first section (11) are titanium, stainless steel, pyrolytic carbon and various plastics. Also, other suitable materials of choice could be used, as well.

The material comprising the second section (15) is flexible and is capable of being affixed to the first section. Preferably, the material is inert or compatible with body tissues. Examples of materials that could be used for the second section include silastic, polyethylene, Dacron and Teflon. Also, other suitable materials of choice could be used, as well.

The annuloplasty ring (10) of the present invention reestablishes the normal shape and contour to the mitral valve annulus (34). The first section (11) of the annuloplasty ring (10) is adjacent to the inter-trigone section (36) after implantation, as shown in FIGS. 1A–1F. The curvature of the bow (70) is oriented to conform to the portion of the mitral valve annulus (34) that is located adjacent to the aortic valve root. Both the first section (11) and the inter-trigone section (36) are substantially rigid. Since the inter-trigone section (36) does not normally bend in response to the movements of the heart, it is, therefore, not required for the first section (11) to bend or flex either.

Figure 4:
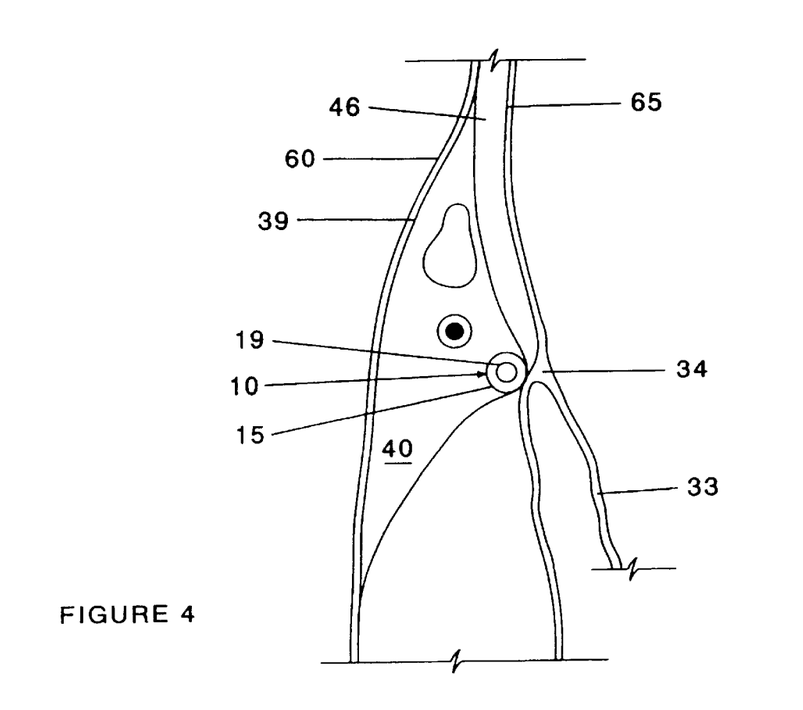
FIG. 4 is a schematic cross sectional side view of a portion of the heart depicting the atrioventricular groove with the annuloplasty ring implanted therein.

The second section (15) is implanted adjacent to the posterior portion (35) of the annulus. Both the posterior portion (35) and the second section (15) are flexible and, as a result, can flex and move with the natural movements of the heart, as the left ventricle relaxes and contracts. Furthermore, the method of implanting the annuloplasty ring within the fat pad (40) of the atrioventricular groove (39), as shown in FIG. 4, ensures that the annulus and the second section (15) of the ring (10) will remain flexible indefinitely.

Referring again to FIGS. 1A–1F, the needle (20) acts as a leader guide to implant the ring (10) in the proper location and position in the atrioventricular groove (39) around the mitral valve annulus (34). The tip (72) of the needle is preferably a round-tip which is sharp enough to penetrate the tissue for implantation, yet blunt enough to maneuver within the atrioventricular groove without damaging critical areas.

The size and shape of the annuloplasty ring (10) can be adjusted. Using the measurement indicia (18) on the second section (15) as a guide, the appropriate length of the section is established, then any unnecessary length on the second section (15) can be removed by cutting, as shown in FIG. 1D. By changing the length of the second section (15), the circumference of the annuloplasty ring is also changed.

Figure 5:
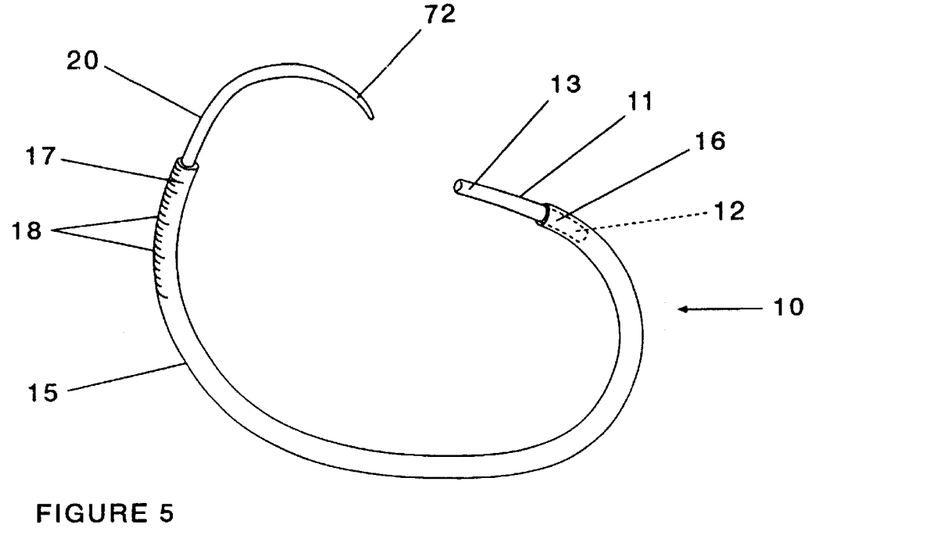
FIG. 5 is a view of the mitral valve annuloplasty ring in a surgical configuration.

As shown in FIG. 2A, the second means for joining the first end of the first section to the proximal end of the second section and the first means for joining the second end of the first section to the distal end of the second section secures the ends (12, 13) of the first section (11) to the respective ends (16, 17) of the second section (15) to form a closed loop. In one preferred embodiment in which the first and second means for joining comprise frictional engagements, the proximal (16) and distal (17) ends of the second section are preferably disposed adjacent to each other at a center region of the first section (11), thereby covering a substantial portion of the first section (11). Alternately, the second end (13) of the first section (11) can be free and unattached while the distal end (17) of the second section (15) is attached to the needle (20) for performing the annuloplasty as shown in FIG. 5.

The length of the first section (11) is shorter than the length of the second section (15). The length of first section (11) can vary, but it is preferred that its length be no more than about 50–75% of the length of the inter-trigone section (36) of the mitral valve annulus being repaired. The requisite proportion for a particular annuloplasty ring will depend on the flexibility of the second section (15). As for example, the more flexible the material forming the second section (15), the longer the length of the first section (11) should be relative to the length of the inter-trigone section (36). Conversely, the less flexible the material of the second section (15), the shorter the relative length of the first section (11) should be relative to the length of the inter-trigone portion (36).

The lengths of the two sections can be varied relative to each other in order to achieve various shapes for the closed loop of the annuloplasty ring (10). For example, by lengthening the first section (11) relative to the length of the second section (15), the annuloplasty ring will become "flatter" as characterized by a smaller anterior to posterior distance.

In one preferred embodiment of the present invention, the first section (11) has a length of approximately 1.5 cm and an overall diameter of approximately 6 mm. The diameter can, however, vary so long as it fits the mitral valve annulus under repair and it precludes inadvertent deformation or breakage of the ring.

In one preferred embodiment, the indicia (18) are markings spaced at intervals of about 1.0 mm. However, the intervals could be spaced at any desired distance, extending for any desired length along the second section (15).

Figure 6:
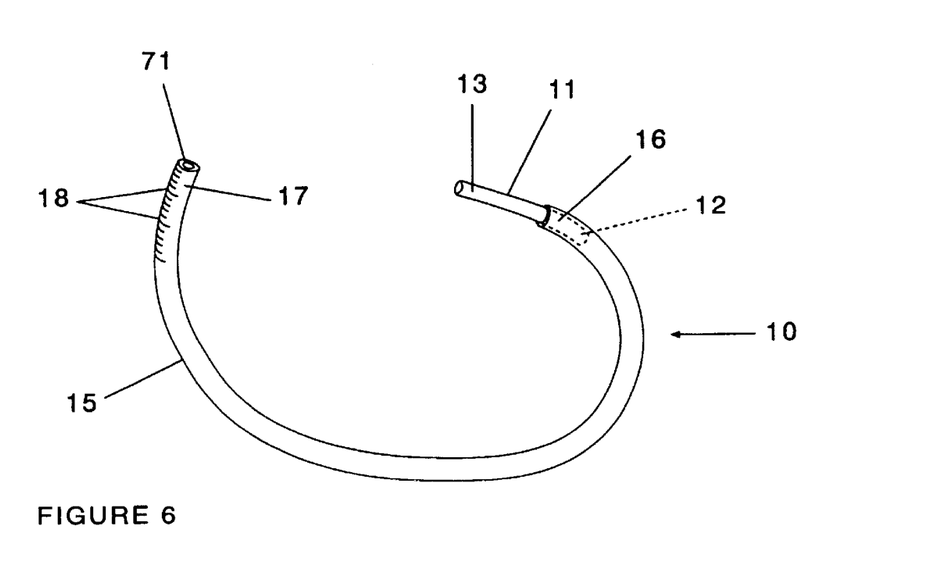
FIG. 6 is a view of the mitral valve annuloplasty ring in an open configuration.

An open configuration of the annuloplasty ring (10) is shown in FIG. 6 wherein the first section (11) has its first end (12) attached to the second section's proximal end (16). The second end (13) of the first section (11) and the distal end (17) of the second section (15) are unattached.

A closed configuration, shown in FIG. 2A, comprises the first end (12) of the first section (11) being attached to the proximal end (16) of the second section (15) and the second end (13) of the first section (11) being attached to the distal end (17) of the second section (15). In the closed configuration, the annuloplasty ring (10) forms the closed loop. After the annuloplasty procedure, the ring (10) is in its closed configuration.

In FIG. 5, the annuloplasty ring (10) of the present invention is shown in a surgical configuration in which the first end (12) of the first section (11) is attached to the proximal end (16) of the second section (15) and the needle (20) is attached to the distal end (17) of the second section (15). The second end (13) of the first section (11) is unattached. The surgical configuration is designated primarily for use during the annuloplasty procedure.

Figure 1A:
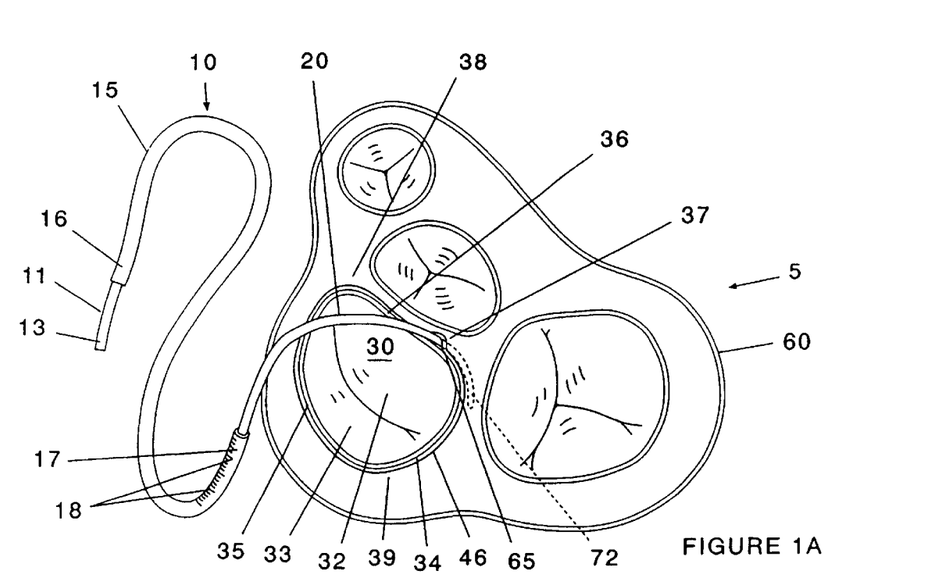
FIGS. 1A–1F are cutaway views of the heart as seen from the atrial position depicting a preferred method of implanting the mitral valve annuloplasty ring in the atrioventricular groove.
Figure 1B:
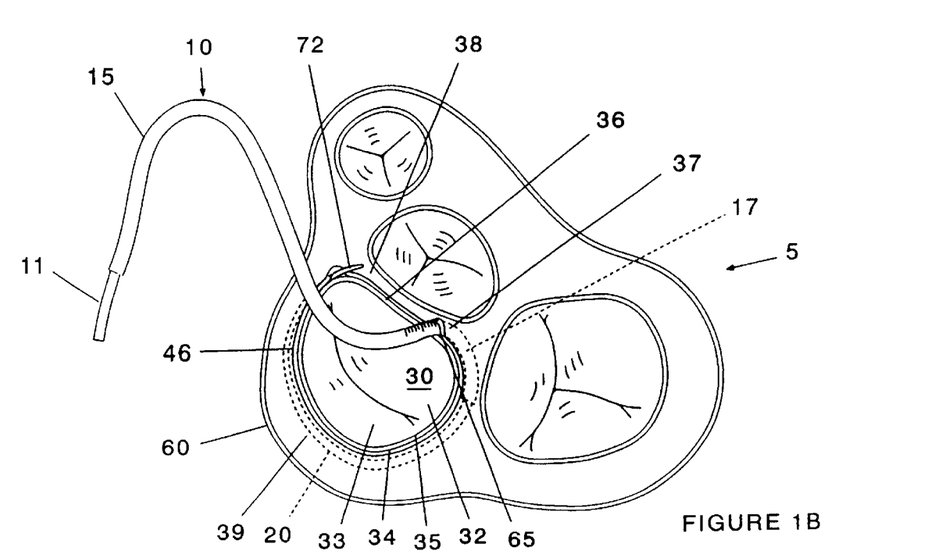
Figure 1C:
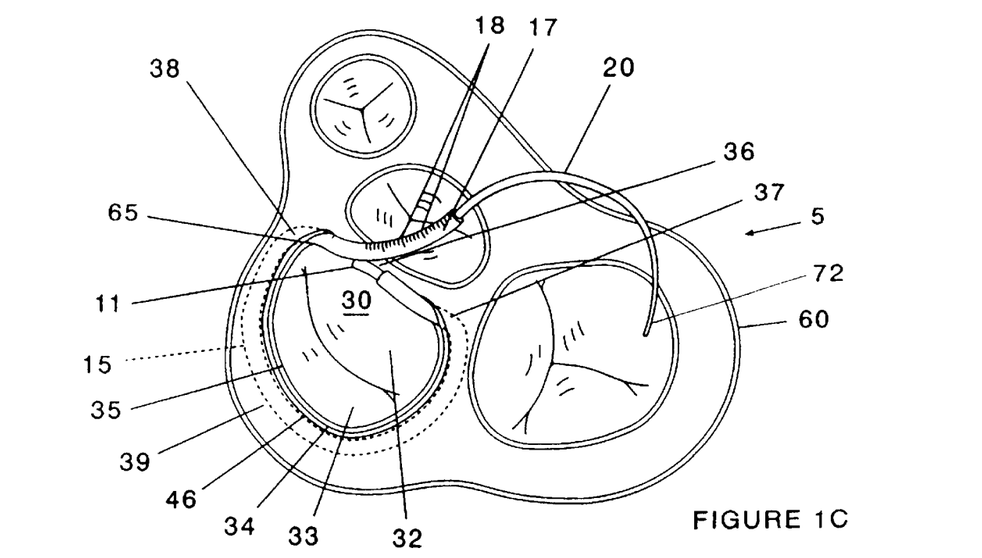
Figure 1D:
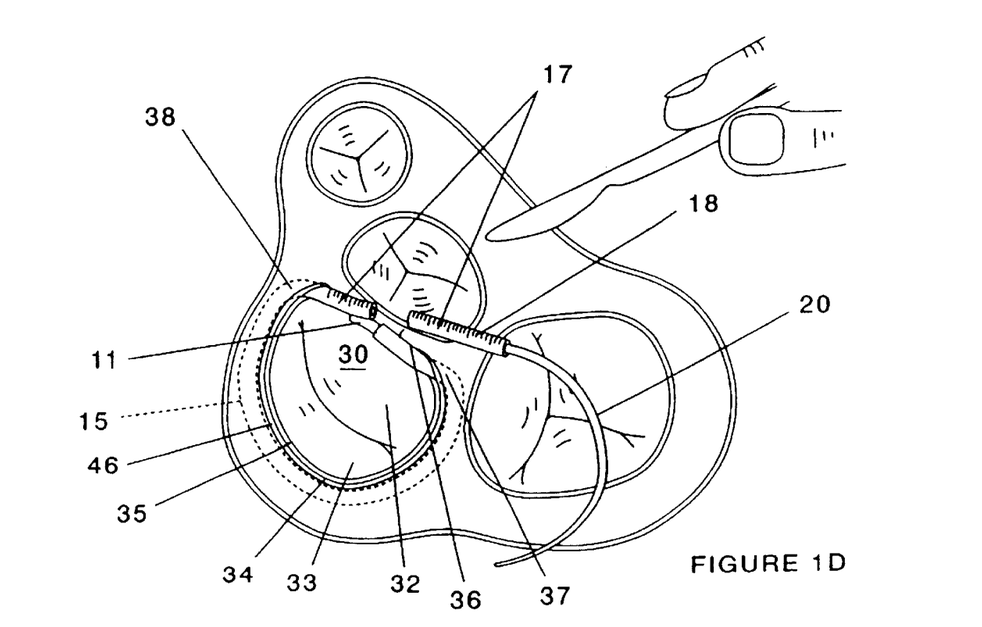
Figure 1E:
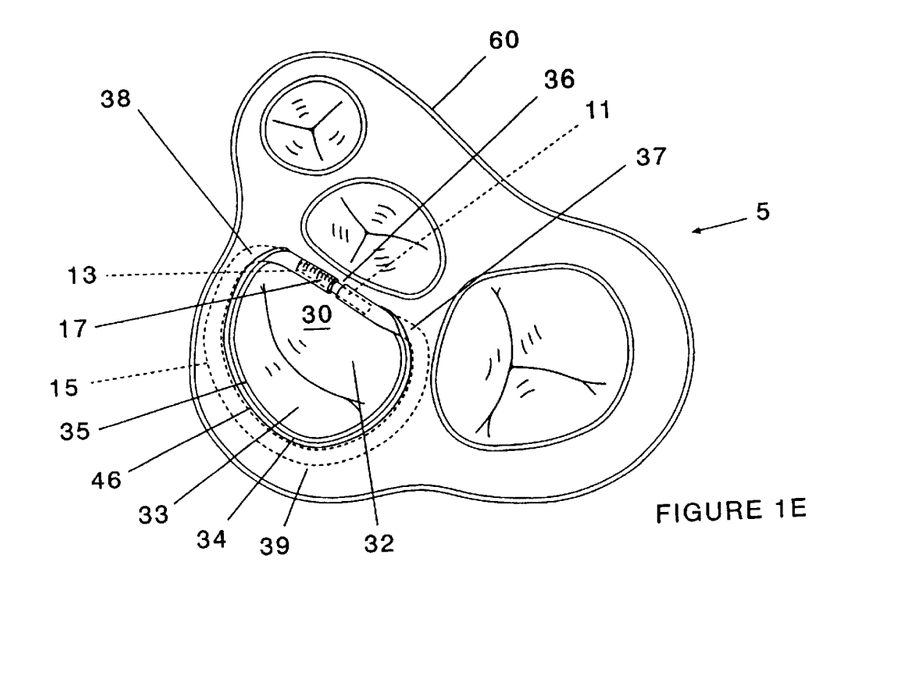

After the annuloplasty ring (10) is implanted as in FIG. 1E, the first section (11) is in alignment with the inter-trigone section (36) of the mitral valve annulus (34) such that the bow (70) conforms to the contour of the annulus (34) adjacent to the aortic valve root. The inter-trigone section (36) which extends between the left (38) and right (37) fibrous trigones is substantially rigid, as is the first section (11) of the ring. The second section (15) is primarily implanted around the posterior portion (35) of the annulus (34) and within the fat pad (40) of the atrioventricular groove (39) as shown in FIG. 4. Along with the posterior portion (35) of the annulus (34), the second section (15) is allowed to move and flex freely with the movements of the heart.

Referring to FIGS. 1A–1E, the annuloplasty ring (10) is installed adjacent to the mitral valve annulus (34) and within the fat pad (40) of the atrioventricular groove (39). After the ring (10) is implanted, the second section (15) is cut to the appropriate size for the patient. The distal end (17) of the second section (15) is then attached to the first section (11). Preferably, the ring (10) is sutured to the annulus at the left and right fibrous trigones. However, this suturing may be avoided if deemed not necessary.

To implant the annuloplasty ring in a patient, the needle (20) is attached to the distal end (17) of the second section (15) and the first end (12) of the first section (11) is attached to the proximal end (16) of the second section (15), as shown in the surgical configuration of FIG. 5. In one preferred embodiment, the needle is attached by inserting its attaching end (73) into the exterior opening (71) of the hollow inner portion (19) of the second section (15).

The tip of the needle (20) is passed through the endocardium (65) and the left atrial myocardial wall (46) from the endocardial aspect at the right fibrous trigone (37), as shown in FIG. 1A, simultaneously pulling the first (11) and second (15) sections of the ring (10) behind it, such that a portion of the second section (15) eventually passes through the left atrial myocardial wall (46) as in FIG. 1B. The needle (20) is passed in a posterior direction just external to and parallel to the mitral valve annulus (34). The tip of the needle (20) is passed around the outside curvature of the mitral valve annulus (34) and within the fat pad (40) of the atrioventricular groove (39). The needle (20) is moved in a clockwise direction towards the left fibrous trigone (38).

At the left fibrous trigone (38), the needle's tip (72) is passed back through the left atrial myocardial wall (46) from the epicardium (60) and back through the endocardium (65) at the left fibrous trigone (38), thereby pulling the first section (11) into position along the anterior portion (36) and pulling the second section (15) into position within the atrioventricular groove (39) such that the second section (15) is adjacent to the posterior portion (35) of the mitral valve annulus (34), as shown in FIG. 1C.

Referring to FIG. 1D, the annuloplasty ring (10) is sized using the measurement indicia (18) to determine the appropriate length of the second section (15) and hence the appropriate circumference for the annuloplasty ring (10). The distal end (17) can be cut to size, if required, by severing the second section (15) at a selected location on the second section (15). The needle (10) can be removed prior to sizing and/or cutting of the second section (15) or, alternately, it can remain attached to the ring (10) during sizing and/or cutting.

The distal end (17) of the second section (15) is then joined to the second end (13) of the first section (11). In one preferred embodiment as shown in FIG. 1E, the second end (13) and distal end (17) are joined by frictional engagement wherein the second end (13) of the first section (11) is inserted into the hollow inner portion (19) of the second section, until the distal (17) and proximal (16) ends of the second section (15) approach one another approximate a center point on the first section (11).

In another embodiment of the method for implanting the annuloplasty ring, the procedure is reversed in direction, wherein the tip (72) of the needle (20) is first passed through the endocardium (65) and the left atrial myocardial wall (46) from the endocardial aspect at the left fibrous trigone (38) and passed in a posterior direction substantially parallel to the annulus (34). The needle (20) is moved in a counter-clockwise direction around the annulus (34) to the right fibrous trigone (37). Here, at the right fibrous trigone (37), the needle's tip (72) is passed back through the left atrial myocardial wall (46) from epicardium (60) and back through the endocardium (65). The procedure then continues as the above procedure is performed in the opposite, counterclockwise direction.

Figure 1F:
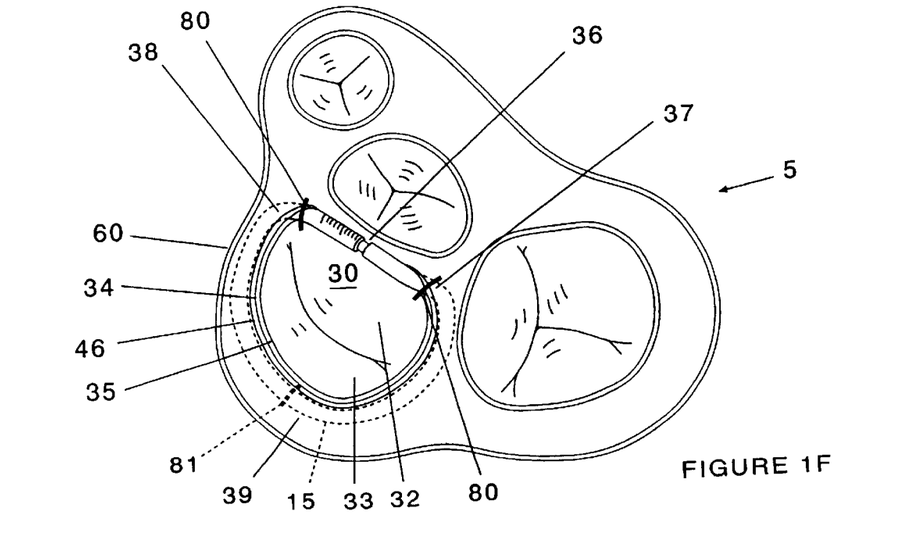

After the annuloplasty ring is in place sutures (80, 81) shown in FIG. 1F can be added to secure the annuloplasty ring to the annulus. A plurality of sutures (80) can be used to fix the ring (10) to the inter-trigone section (36), preferably at the left and right fibrous trigones. Since the inter-trigone section (36) is substantially rigid in the native mitral valve annulus, any scarring that may result from these sutures (80) would not substantially interfere with the normal flexing of the rest of the annulus and movement of the left ventricle.

In addition, at least one suture (81) may be used to fix the second section (15) within the atrioventricular groove (39) as an added precaution for guarding against possible slippage of the ring (10) after it is implanted. This suture (81) would preferably be located near the midpoint of the second section (15).

The preferred embodiments of the present invention allow the mitral valve annulus to maintain its normal flexure, which in turn enables the left ventricle to move in a normal manner as it contracts and relaxes. Furthermore, the method of implanting allows the annuloplasty ring and the annulus, as well, to maintain flexibility indefinitely after the annuloplasty, since it is not necessary to secure the ring in place with a line of sutures through the mitral valve annulus tissue of the posterior portion.

The ring further reestablishes the normal shape and contour of the mitral valve annulus which allows for effective coaptation of the anterior and posterior leaflets of the valve. Additionally, the size and shape of the ring can be adjusted making it easily adaptable to different patients.

In one example, the annuloplasty ring of the present invention can be manufactured using a flexible material that is also elastic to comprise the second section. The elasticity of the ring would accommodate the expansion of the mitral annulus during relaxation of the left ventricle and accommodate contraction of the annulus during contraction of the left ventricle. In other words, the annulus would expand and contract, in addition to flexing, with the expansion and contraction of the left ventricle.

In another example, the first (11) and second (15) sections are joined integrally at the respective first (12) and proximal (16) ends, wherein the first section remains substantially rigid and the second section (15) remains flexible. The integral joining of the two sections can be done by coextrusion, molding or other suitable manufacturing techniques of choice.

Although the present invention has been described in considerable detail with reference to certain preferred versions thereof, other versions are possible. Therefore, the spirit and scope of the appended claims should not be limited to the description of the preferred versions contained herein.

What is claimed is:

1. An annuloplasty for repairing a valve in a patient's heart, said annuloplasty ring comprising:
   (a) a first section for implanting adjacent to the valve; and
   (b) a second flexible section for implanting within a fat pad of an atrioventricular groove in the heart.

2. The annuloplasty ring of claim 1, wherein said second flexible section comprises a proximal end and a distal end and a means for joining the distal end to a needle.

3. The annuloplasty ring of claim 2, further comprising a needle having an attaching end with an outer diameter.

4. The annuloplasty ring of claim 3, wherein said means for joining the distal end to the needle comprising a frictional engagement.

5. The annuloplasty ring of claim 4, wherein said first section comprises first and second ends, said first and second ends each having an outer diameter;
   said annuloplasty ring further comprising:
   (a) first means for joining the distal end of the second flexible section to the second end of the first section; and
   (b) second means for joining the proximal end of the second flexible section to the first end of the first section.

6. The annuloplasty ring of claim 5, further comprising:
   (a) an open configuration wherein said first section is attached to said second section by said second means for joining, and said second end of said first section and said distal end of said second flexible section are unattached;
   (b) a closed configuration wherein said first section is attached to said second section by said first and second means for joining, thereby forming a loop; and
   (c) a surgical configuration wherein said first section is attached to said second section by said first means for joining, and said second flexible section is attached to the needle by said means for joining said distal end of said second flexible section to said needle.

7. The annuloplasty ring of claim 5, wherein said first means for joining comprises a frictional engagement and said second means for joining comprises a frictional engagement.

8. The annuloplasty ring of claim 7, wherein said distal and proximal ends each include a hollow inner portion having an inner diameter, said outer diameters of said first and second ends are approximately equal to said inner diameter of said hollow inner portion, and said frictional engagement of said first means for joining is between said inner diameter of said hollow inner portion at said distal end and said outer diameter of said second end, and said frictional engagement of said second means for joining is between said inner diameter of said hollow inner portion at said proximal end and said outer diameter of said first end.

9. The annuloplasty ring of claim 4, wherein the distal end of the flexible section further comprises a hollow inner portion with an inner diameter approximately equal to the outer diameter of the attaching end of the needle and said frictional engagement is between said inner diameter and said outer diameter of the attaching end.

10. The annuloplasty ring of claim 1, wherein said first section is rigid with first and second ends being substantially straight, said first section further having a bow between the first and second ends.

11. The annuloplasty ring of claim 1, further comprising a means for sizing the ring.

12. The annuloplasty ring of claim 1, wherein said first section comprises an outer diameter of approximately 6 mm.

13. An annuloplasty ring for use in an annuloplasty surgical procedure to correct mitral insufficiency in a patient by restoring the mitral valve annulus to a normal shape and flexibility which is determined by the movement of the left ventricle, the mitral valve and the mitral valve annulus, wherein said annuloplasty ring comprises:
   a first rigid section having a first end, a second end and a length, said first and second ends having an outer diameter;
   a second flexible section having a distal end, a proximal end, a length, means for sizing the ring, and at least one hollow inner portion with an inner diameter and an exterior opening at the proximal and distal ends;
   a round-tip needle having a tip and an attaching end with an outer diameter;
   first means for joining the distal end of the second section to the second end of the first section;
   second means for joining the proximal end of the second section to the first end of the first section;
   third means for joining the distal end of the second section to the needle;
   wherein said outer diameter of the first section and the outer diameter of the attaching end are approximately equal to the inner diameter of the hollow inner portion and said length of said second flexible section is greater than said length of said first rigid section;
   said first means for joining comprising a frictional engagement between the inner diameter of the hollow inner portion at the distal end and the outer diameter of the second end, said second means for joining comprising a frictional engagement between the inner diameter of the hollow inner portion at the proximal end and the outer diameter of the first end, and said third means for joining comprising a frictional engagement between the inner diameter of the hollow inner portion at the distal end and the outer diameter of the attaching end of the needle;
   said means for sizing the ring further comprising measurement indicia on the distal end of the second section;
   said first rigid section is substantially straight and further comprises a bow positioned between the first and second ends;
   the annuloplasty ring further comprising:
   (1) an open configuration defined by said first section being joined to said second section by said second means for joining, wherein the exterior opening and hollow inner portion at the proximal end of the second section receive the first end of the first section therein, the first end and the proximal end are held together by said frictional engagement, and said second end and said distal end being unattached;
   (2) a surgical configuration defined by said first section being joined to said second section by said second means for joining and said second section being joined to said needle by said third means for joining, wherein said exterior opening and hollow inner portion at the proximal end of the second section receive the first end of said first section therein, the first end and proximal end are held together by said frictional engagement of said second means for joining, and the exterior opening and hollow inner portion at the distal end of the second section receive the attaching end of the needle therein, the distal end and the attaching end are held together by said frictional engagement of said third means for joining; and (3) a closed configuration defined by said first section being joined to said second section by said first and second means for joining, wherein the exterior opening and the hollow inner portion at the proximal end of said second section receive the first end of said first section therein, the proximal end and the first end are held by said frictional engagement of said second means for joining, and said exterior opening and the hollow inner portion at the distal end of the second section receive the second end of the first section therein, the distal end and the second end are held by said frictional engagement of said first means for joining;

wherein said first rigid section is adapted for implantation adjacent to an anterior portion of the mitral valve annulus, and said second section is adapted for implantation in the fat pad of the atrioventricular groove.

14. A kit for an annuloplasty ring to be used in an annuloplasty surgical procedure to correct mitral insufficiency in a patient by restoring the mitral valve annulus to a normal shape and flexibility which is determined by the movement of the left ventricle, the mitral valve and the mitral valve annulus, wherein said annuloplasty ring comprises:

a first rigid section having a first end, a second end, a length and an outer diameter;

a second flexible section having a distal end, a proximal end, a length, means for sizing the ring, and at least one hollow inner portion with an inner diameter and an exterior opening at the distal and proximal ends;

a round-tip needle having a tip and an attaching end with an outer diameter;

first means for joining the distal end of the second section to the second end of the first section;

second means for joining the proximal end of the second section to the first end of the first section;

third means for joining the distal end of the second section to the needle;

wherein said outer diameter of the first section and the outer diameter of the attaching end are approximately equal to the inner diameter of the hollow inner portion;

said first means for joining comprising a frictional engagement between the inner diameter of the hollow inner portion at the distal end and the outer diameter of the second end when the two ends are joined; said second means for joining comprising a frictional engagement between the inner diameter of the hollow inner portion at the proximal end and the outer diameter of the first end when the two ends are joined; and said third means for joining comprising a frictional engagement between the inner diameter of the hollow inner portion at the distal end and the outer diameter of the attaching end of the needle when the two ends are joined.

15. A kit for an annuloplasty ring comprising:

a first section;

a second flexible section having proximal and distal ends;

means for joining the distal end of the second flexible section to a needle; and means for sizing the annuloplasty ring.

16. A kit for an annuloplasty ring comprising:

a first section having first and second ends, said first and second ends each having an outer diameter;

a second flexible section having proximal and distal ends;

means for joining the distal end of the second flexible section to the needle;

a needle having an attaching end for attachment to the second flexible section;

first means for joining the distal end of the second flexible section to the first section; and second means for joining the proximal end of the second flexible section to the first section.

17. The kit for an annuloplasty ring in claim 16, wherein said means for joining the distal end of the second flexible section to a needle comprising a frictional engagement.

18. The kit for an annuloplasty ring in claim 17, wherein said first means for joining comprises a frictional engagement and said second means for joining comprises a frictional engagement, said second flexible section includes a hollow inner portion at the distal and proximal ends, said hollow inner portion having an inner diameter approximately equal to the outer diameters of the first and second ends of the first section;

wherein said frictional engagement of said first means for joining is between said inner diameter of said hollow inner portion at said distal end and said outer diameter of said second end, and said frictional engagement of said second means for joining is between said inner diameter of said hollow inner portion at said proximal end and said outer diameter of said first end.

19. The kit for an annuloplasty ring of claim 17, wherein the distal end of the second flexible section further comprises a hollow inner portion with an inner diameter approximately equal to the outer diameter of the attaching end of the needle and said frictional engagement of said means for joining the distal end to a needle is between said inner diameter and said outer diameter of the attaching end.

20. The annuloplasty ring of claim 16, wherein said first section having first and second ends, said annuloplasty ring further comprising:

an open configuration wherein said first end of the first section is attached to said proximal end of the second flexible section by said second means for joining, and said second end of said first section and said distal end of said second flexible section are unattached;

a closed configuration wherein said first section is attached to said second section by said first and second means for joining, thereby forming a loop; and a surgical configuration wherein said first end of the first section is attached to said proximal end of the second flexible section by said second means for joining, and said distal end of the second flexible section is attached to a needle by said means for joining the distal end of the second flexible section to a needle.

* * * * *

UNITED STATES PATENT AND TRADEMARK OFFICE
CERTIFICATE OF CORRECTION

PATENT NO.     : 6,565,603 B2
DATED          : May 20, 2003
INVENTOR(S)    : James L. Cox It is certified that error appears in the above-identified patent and that said Letters Patent is hereby corrected as shown below:

Column 3,
Before line 1, insert the following paragraph -- It is a further object of the present invention to provide an annuloplasty ring that assumes the shape of the normal mitral valve annulus to allow for effective functioning of the valve. --
Lines 10-14, the paragraph should read -- It is a further object of the present invention to provide an annuloplasty ring that allows the base of the left ventricle to assume its full range of movement when contracting and relaxing to allow effective functioning of the left ventrile. --
Lines 32-35, this paragraph should be moved to be under line 36 the heading "BRIEF DESCRIPTION OF THE DRAWINGS".

Signed and Sealed this

Third Day of February, 2004

JON W. DUDAS
*Acting Director of the United States Patent and Trademark Office*